(12) United States Patent
Viswanathan (10) Patent No.: US 7,627,361 B2
(45) Date of Patent: Dec. 1, 2009

(54) METHODS AND APPARATUS FOR STEERING MEDICAL DEVICE IN BODY LUMENS

(75) Inventor: Raju R. Viswanathan, St. Louis, MO (US)

(73) Assignee: Stereotaxis, Inc., St. Louis, MO (US)

(*) Notice: Subject to any disclaimer, the term of this patent is extended or adjusted under 35 U.S.C. 154(b) by 881 days.

(21) Appl. No.: 11/211,155

(22) Filed: Aug. 23, 2005

(65) Prior Publication Data

US 2006/0074297 A1    Apr. 6, 2006

Related U.S. Application Data

(60) Provisional application No. 60/604,101, filed on Aug. 24, 2004.

(51) Int. Cl.
*A61B 5/05* (2006.01)

(52) U.S. Cl. ............... 600/424; 600/407; 600/427; 128/899

(58) Field of Classification Search ......... 600/407, 600/417, 424, 431, 427, 117, 373, 508; 606/108, 606/130; 128/897, 898, 899; 324/207.13, 324/207.22, 260
See application file for complete search history.

(56) References Cited

U.S. PATENT DOCUMENTS

| | | | |
|---|---|---|---|
| 6,015,414 A | 1/2000 | Werp et al. | |
| 6,157,853 A | 12/2000 | Blume et al. | |
| 6,241,671 B1 | 6/2001 | Ritter et al. | |
| 6,292,678 B1 | 9/2001 | Hall et al. | |
| 6,304,768 B1 | 10/2001 | Blume et al. | |
| 6,330,467 B1 | 12/2001 | Creighton, IV et al. | |
| 6,401,723 B1 | 6/2002 | Garibaldi et al. | |
| 6,507,751 B2 | 1/2003 | Blume et al. | |
| 6,522,909 B1 | 2/2003 | Garibaldi et al. | |
| 6,630,879 B1 | 10/2003 | Creighton, IV et al. | |
| 6,702,804 B1 | 3/2004 | Ritter et al. | |
| 6,755,816 B2 | 6/2004 | Ritter et al. | |
| 7,019,610 B2 | 3/2006 | Creighton, IV et al. | |
| 2003/0125752 A1* | 7/2003 | Werp et al. ............... | 606/108 |
| 2004/0064153 A1 | 4/2004 | Creighton, IV et al. | |
| 2004/0158972 A1 | 8/2004 | Creighton, IV et al. | |
| 2004/0249262 A1 | 12/2004 | Werp et al. | |
| 2004/0249263 A1 | 12/2004 | Creighton, IV | |
| 2004/0260172 A1 | 12/2004 | Ritter et al. | |

* cited by examiner

*Primary Examiner*—Brian Casler
*Assistant Examiner*—Nasir Shahrestani
(74) *Attorney, Agent, or Firm*—Harness, Dickey & Pierce, P.L.C.

(57) ABSTRACT

A method of operating a navigation system that can orient the distal end of a medical device in a selected direction to navigate the medical device through a network of body lumens in an operating region in a subject that includes identifying a path through the network of body lumens in the operating region; displaying a two-dimensional image of the operating region including the path through the body lumens; determining at least one location on the path; and operating the navigation system to orient the distal end of the medical device in a direction substantially aligned with the path at the at least one location and advancing the distal end of the medical device.

29 Claims, 4 Drawing Sheets

METHODS AND APPARATUS FOR STEERING MEDICAL DEVICE IN BODY LUMENS

CROSS-REFERENCE TO RELATED APPLICATIONS

This application claims benefit of U.S. Provisional Patent Application Ser. No. 60/604,101, filed Aug. 24, 2004, the entire disclosure of which is incorporated herein by reference.

BACKGROUND OF THE INVENTION

This invention relates to the navigation of medical devices in the body, and in particular to methods of and apparatus for steering medical devices in body lumens such as blood vessels.

This invention relates to the navigation of medical devices in the body, and in particular to methods of and apparatus for steering medical devices in body lumens such as blood vessels.

Automated or semi-automated medical device navigation has recently emerged as a major advancement in medical technology. Once such form is magnetic navigation, in which external magnets apply a magnetic field of a selected direction to an operating region in a subject to orient the distal end of a magnetically responsive medical device in the operating region. Other forms of remote navigation include systems employing mechanical and electrostrictive movement to remotely orient the distal end of the medical device.

While these technologies, and in particular magnetic navigation technology, are well developed, improvement can still be made in the ways these navigations systems are controlled to orient the distal end of the medical device in the appropriate orientation. In particular it is desirable facilitate the control of navigation systems for quick and easy navigation along a desired path through a body lumen, such as through the subject's vasculature.

SUMMARY OF THE INVENTION

Generally methods and apparatus of the present invention provide for control of a remote navigation system for intuitive and quick steering of a medical device along a path through a subject's vasculature, with a high level of system automation. This invention is particularly useful for magnetic navigation system, but the invention is not so limited, and can be applied to any remote navigation systems that can orient the distal end of a medical device in a selected direction to navigate the medical device through a body lumen.

One embodiment of a method in accordance with the principles of this invention, comprises identifying a path through a portion of the vasculature in an operating region in a subject. The current location of the distal end of the medical device is determined and the direction of the path at the location is determined. The navigation system is then operated to orient the distal end of the medical device in the determined direction of the path at the determined current location and the medical device is advanced.

The path can be identified in a variety of ways, including but not limited to identifying points on the path on at least two images of the operating region or identifying lines on the path on at least two images of the operating region or by using image processing of suitably contrast-enhanced images.

The current location of the distal end of the medical device is preferably determined from image processing, but it could also be determined from any suitable medical localization system, including but not limited to magnetic, ultrasonic or electrostatic localization systems. The current location can also be determined knowing the path and the length of the device in the path.

The distal end of the medical device is advanced by manually advancing the proximal end of the medical device, using a machine under the manual control of a physician or under the automated control of a computer to advance the proximal end of the medical device.

In one preferred embodiment of the method, the location is repeatedly determined, and the direction of the path at the determined location (the desired orientation of the medical device) determined for each location, and the navigation system operated to orient the distal end of the medical device in the desired orientation. The distal end of the device can be advanced continuously or in a step wise mode. In the continuous mode, the speed of advancement may be constant, or the speed may be adjusted, for example based on the rate of change of the direction of the path, or the rate of change of the orientation of the distal end of the medical device. In the step wise mode, the distal end of the medical device can be advanced for a discrete time interval or a discrete distance interval, and the location of the medical device and desired direction of the distal end of the medical device determined after each interval. These intervals can be constant, or they can change, for example depending on the curvature of the path, or the rate of change of the orientation of the distal end of the medical device.

Thus, the methods of this invention provide for the control of medical navigation systems, and facilitate the navigation of medical devices along planned paths through body lumens, such as a subject's vasculature. These and other feature and advantages will be in part apparent and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENTS

The devices and methods of this invention facilitate the use of remote navigation systems, such as magnetic navigation systems, to navigate medical devices through body lumens, such as the vasculature. While the devices and methods are described particularly in the context of a magnet navigation system, the invention is not so limited, and is applicable to any navigation system that can remotely orient the distal end of a medical device in a selected direction.

Generally, a preferred embodiment of a method in accordance with the principles of this invention comprises identifying a path through a body lumen in an operating region, such as the subject's vasculature. The current location of the distal end of the medical device is determined, and from this the direction of the path and the determined current location is determined. The remote navigation system is then operated to orient the distal end of the medical device in the determined direction, and the distal end of the medical device is advanced along the path.

In the preferred embodiment, the path can be quickly and easily identified by identifying points on the path on at least two images of the operating region. The path can also be identified by identifying lines on the path on at least two images of the operating region. These points or lines can be reconstructed into a continuous three dimensional path using well known mathematical techniques and algorithms such as spline-based reconstructions. Alternatively the reconstruction of the path can be performed through the use of image processing, as is done in commercially available software such as CardiOp, manufactured by Paieon, Inc.

In a preferred embodiment, the current location of the distal end of the medical device is also determined. In the preferred embodiment, this is conveniently done through image processing. However, the location of the distal end of the medical device can also be determined with a remote medical localization system, including but not limited to RF, magnetic, ultrasonic, or electrostatic localization systems. The location of the distal end of the medical device can also be determined by dead reckoning, since the path of the device is known, and the length of the device is measured, the position of the distal end can be calculated.

With the desired path known, image processing of a single plane image of the operating region can quickly and easily locate the distal end of the device. Once the current location of the distal end of the medical device has been determined, the direction of the desired path at the location can be determined. Once the direction of the desired path is determined, the remote navigation system can be controlled to orient the distal end of the medical device in the desired direction. At least in the case of a magnetic system, where because of device properties such as stiffness, the actual position of the device may lag from the direction of the applied magnetic field, this orientation preferably takes into account the physical properties of the device, so that a magnetic field is applied to cause the medical device to orient in the desired direction, rather than simply applying a magnetic field in the desired direction. With other navigation systems, the device properties are preferably also taken into account so that the distal end of the device aligns with the desired path.

Once the distal end of the medical device is aligned with the desired path, the distal end of the device can be advanced. The device can be quickly and easily advanced by manually pushing the proximal end of the device. The device can also be quickly and easily advanced by using an advancement mechanism under manual control. However, in the preferred embodiment the distal end of the device is advanced using an advancement mechanism under automated control.

In the preferred embodiments the determination of the current location of the distal end of the medical device and the determination of the direction of the path at the current location is performed repeatedly. In one preferred embodiment these steps are performed continuously or nearly continuously. In another preferred embodiment these steps are performed at discrete intervals. In either embodiment, the advancement of the distal end of the medical device is preferably coordinated with the steps of determining the position, determining the direction, and orienting the distal end of the medical device.

In a continuous mode, the advancement can be continuous. The advancement can be at a constant speed, or the speed can be adjusted, for example based on the local degree of curvature of the path, or the rate of change of the direction of the distal end of the medical device. Where the direction of the path is changing or the direction of the device is changing, the advancement can slow to accommodate the changes to the orientation of the device, and where the direction of the path is relatively constant or the direction of the device is not changing, the advancement can be relatively fast.

In the step wise mode, the advancement can be for a fixed time interval or for a fixed distance interval. These intervals can be constant, or the intervals can be adjusted, for example based on the local degree of curvature of the path, or the rate of change of the direction of the distal end of the medical device. Where the direction of the path is changing or the direction of the device is changing, the intervals can be decreased to accommodate the changes to the orientation of the device, and where the direction of the path is relatively constant or the direction of the device is not changing, the intervals can increase.

In some embodiments it may be desirable to precess the distal end of the medical device, i.e. orient the device other than along the centerline of the desired path. This can be helpful in avoiding static friction, and more importantly to help avoid obstructions in the body lumen and find a pathway through such obstructions or occluded regions. The precession of the distal end of the device can be automatic and can be random, or it can be implemented for example where the distal end encounters an obstruction (which is detected by a failure of the distal end to move in response to advancement of the medical device). A control algorithm can be implemented that moves the distal end of through a series of different angular orientations to try to pass by the obstruction. This control algorithm can be a "smart" algorithm that using location orientation information, takes into account likely locations of obstructions and starts in directions that are least likely to be obstructed.

In one preferred embodiment instead of characterizing a single path in the operating region, the user characterizes a portion of the vasculature. This can be done in the same manner that the path is identified above. The user then identifies a target location in the vasculature, and a path from the current location to the target location is determined. Then the method proceeds substantially as described above.

In another preferred embodiment instead of using an actual planned path, an idealized anatomical model can be used. Because of gross structural similarities between subject anatomies, a model often provides a suitable idealized desired path for many navigations. The user identifies the current location and the target location on a display of the anatomical model, and the path between the current location and the desired location on the model is used. In this embodiment, the user would simply identify a location on the path where device distal tip alignment with the path is desired, so that the device can be easily maneuvered locally, and the navigation system would then apply a suitable set of actuation controls.

In an alternate preferred embodiment, the user could identify a location on a path that has been determined by (i) marking a set of points or lines on at least a pair of Fluoro images, (ii) image processing a set of contrast enhanced Fluoro images or (iii) extraction from a three dimensional dataset obtained from either a preoperative scan or an intraoperative scan. In the latter case rotational angiography, CT or MR scanning technologies could be employed to obtain the three dimensional dataset. Once the location on the path is identified, the navigation system would apply a set of controls that would substantially align the distal tip of the device with the path direction at the selected location, just as could also be done with an idealized anatomical model. In the case of a magnetic navigation system, for example, the navigation system would apply an appropriate magnetic field direction that would cause device tip alignment with the local path direction, preferably taking into account the physical properties of the device.

In the following technical description vascular paths are used as an example for illustration purposes only, it being understood that the teachings herein are applicable to other body lumens as well.

Characterizing the Vasculature in the Operating Region

Figure 1:
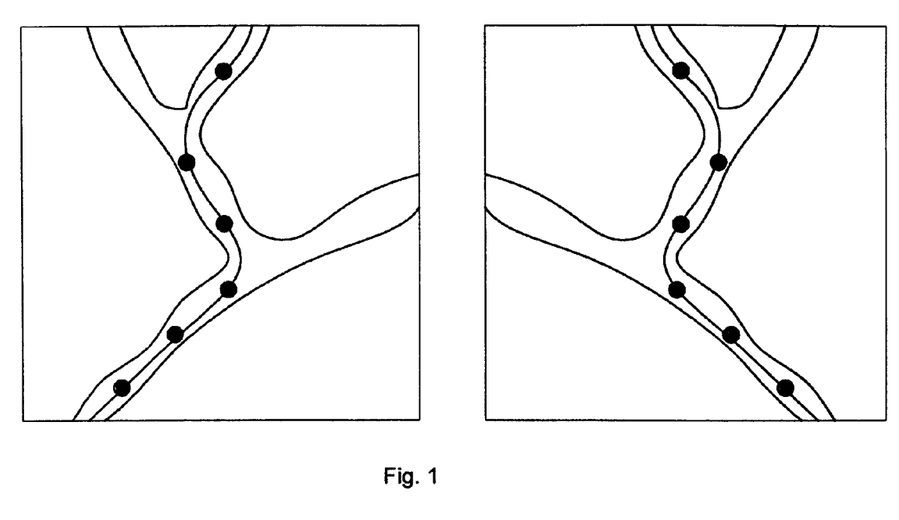
FIG. 1 is a schematic drawing illustrating the definition of a desired path through the vasculature on biplane imaging of the operating region.
Figure 2:
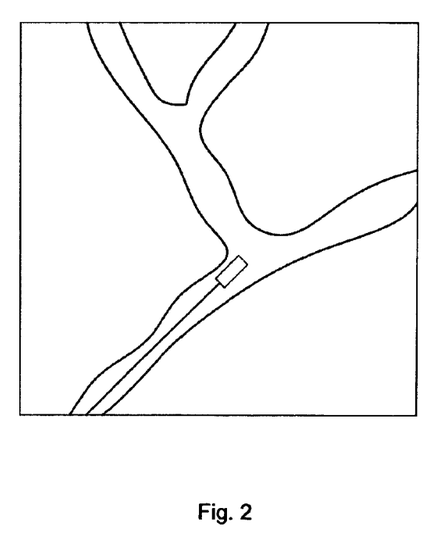
FIG. 2 is a schematic drawing illustrating the identification of the location of the distal end of the device through image processing.
Figure 3:
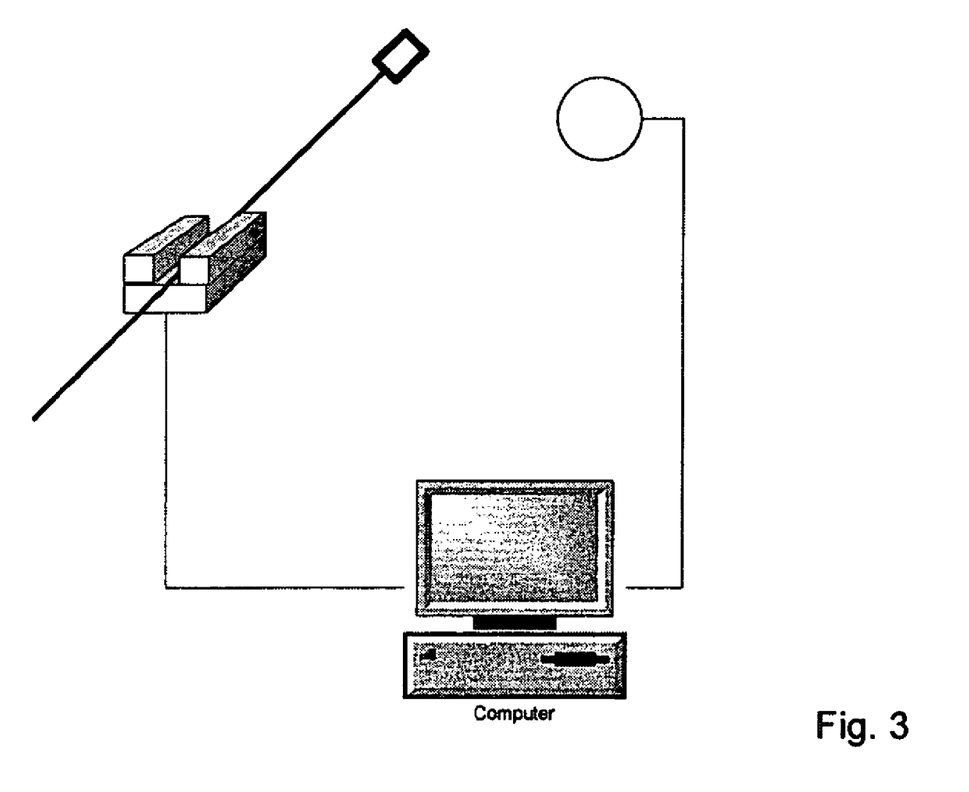
FIG. 3 is a schematic drawing illustrating the identification of the location of the distal end of the device by tracking device advancement.

Given a pair of x-ray images of a patient's vasculature (taken with contrast imaging), a navigation pathway through the vasculature to access a selected location can be defined as follows:

The user either clicks on a small discrete set of points in each image, or draws a path in each image, by clicking or dragging with a mouse or pen-table, or other suitable input-output device, preferably in a predetermined direction (e.g. from the proximal end to the distal end of the path) as shown in FIG. 1.

The system uses a suitable algorithm to reconstruct the three dimensional configuration of the desired path. Where a user sketches a rough path, image processing may be used to reconstruct an accurate path in three dimensions. Alternatively, the contrast enhanced images can be suitably image processed to extract the path.

Once the three dimensional vascular path is defined, the device can be navigated as follows: First the location of the distal end of the medical device is determined. This can be done with a localization system, such as a magnetic localization system, or an ultrasound ultrasonic localization system, or a electrostatic localization system, but it is preferably done with image processing of images (e.g. x-ray or fluoroscopic) images of the operating region. For this purpose, a single x-ray image is sufficient because the three dimensional path through the vasculature has already been already been reconstructed, and the distal end of the medical device is constrained by this vasculature. Alternatively, the user can simply pick the current or a desired device location on the path. Thus, the location of the distal end of the medical device along the path is known.

Using the physical properties of the medical device, together with the known geometry of the path, suitable control variables for the navigation system to orient the distal end of the medical device in the desired direction can be computed and applied to the navigation system. For example, in the case of a magnetic navigation system, using the physical properties of the medical device, together with the known geometry of the path, the direction of the magnetic field required to orient the distal end of the medical device in the desired direction can be determined. This magnetic field direction can then be communicated to the magnetic navigation system, which can apply the desired magnetic field. In the case of other navigation systems, with the known geometry of the path, the desired direction of the distal end of the medical device can be determined, and this information can be communicated to the navigation system, which can orient the distal end of the medical device in the desired direction. Thus the example of magnetic navigation described below is given for illustrative purposes only.

The device can then be advanced, either manually, by pushing the proximal end of the device or with the assistance of an advancement mechanism which pushes proximal end of the device under the direct control of the physician. Alternatively, the device can be advanced automatically with the assistance of an advancement mechanism which pushes the proximal end of the medical device under computer control. The computer can operate the advancement mechanism for a predetermined time, or to advance the distal end a predetermined distance, or the computer can compute an advancement amount based upon the difference between the current orientation and the local direction of the path, or since the device is constrained in the vasculature, the computer can advance the distal end until it reaches a branch or bend in the vasculature, where the orientation of the distal end may need to be changed.

As the distal end of the magnetic medical device is advanced, the new tip location can be automatically determined from image processing, and a new tip orientation can be determined. The system can operate in a step mode, or in a continuous mode. In the step mode, the navigation system is controlled to orient the distal end of the device in the direction of the path, and the distal end of the device is advanced a predetermined amount, the new desired direction at the new location of the distal end is determined, the navigation system is controlled to orient the distal end of the device in the direction of the path, and the distal end of the device is again advanced, and the process continues in a stepwise manner. The steps can be uniform in size, whether measured in time or distance, or they can be dynamically adjusted for example, depending on the rate of change of the direction of the path and/or the proximity to branches in the vasculature.

In the continuous mode, the system continuously updates the position of the distal tip (either through image processing or by calculating the advancement knowing the path and knowing the amount of advancement), calculates the desired orientation at the location, and controls the navigation system accordingly. The rate of advancement can be constant, or the rate can dynamically change, for example depending on the rate of change of the direction of the path and/or the proximity to branches in the vasculature.

Thus, the distal end of the device can be steered in a tight feedback loop in an intuitive manner.

Once the desired path has been quickly marked or defined, for example using an optimal set of x-ray angulations, the device can be steered in an automated manner, even from a single x-ray view that need not be optimal. The user can advance the device, or advancement can be automated with an advancing device.

In an alternate embodiment, rather than using image processing, the device length along the desired path can be measured with the use of a suitable tracking device. From length differences as measured by the tracking device, the length of the device (and thus the location of the distal end of the device) along the path is known, and a computer can suitably control the navigation device to steer the device along the desired path.

In yet another embodiment, the user simply selects a location on the path where a good alignment of the device with the centerline is desired and the system correspondingly orients the device by suitable actuation.

Figure 4:
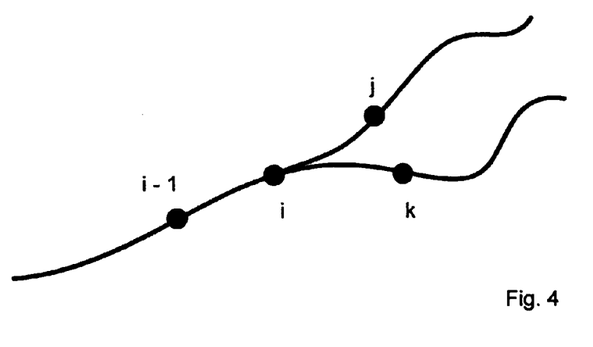
FIG. 4 is a schematic drawing of a branched vessel in a subject's vasculature.

As shown in FIG. 4, a given vasculature path or tree structure is defined by centerline tree. This centerline tree can be defined by a set of points or nodes (which could be derived from spline representations, if available) separated by spaces. These can be derived from image processing, for example using the systems and methods available from Paieon, Inc., or these can be derived from idealized vascular models. These spaces need not be regular and could for example increase and decrease depending upon the curvature of the path. In a preferred embodiment, a spacing of about 2 mm is satisfactory. The nodes are arranged hierarchically, such that each node is tied to its antecedent. A unique proximal node exists for each tree structure since the point of entry for devices into, for instance, the coronary vessels is standard.

Figures 5, 6:
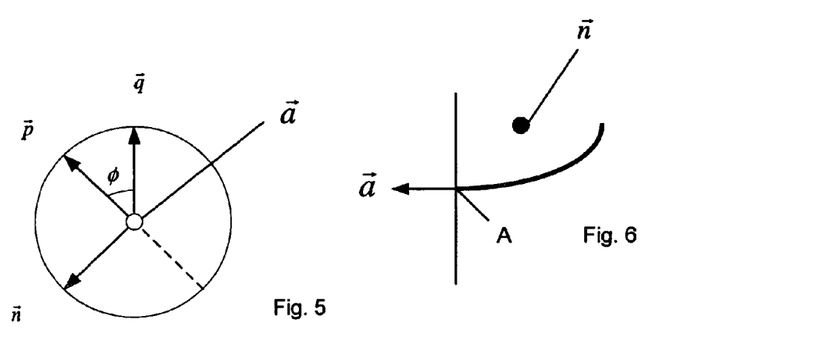
FIG. 5 is a schematic drawing of a medical device in a vessel, transverse to the axis of the vessel.
FIG. 6 is a schematic drawing of a medical device in a vessel, from the side.
Figure 7:
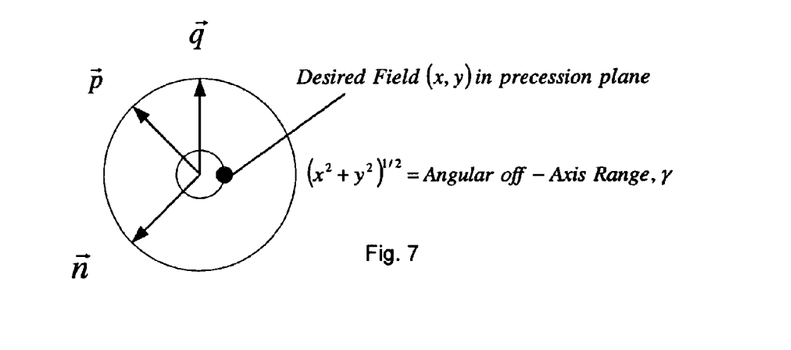
FIG. 7 is a schematic drawing of a medical device in a vessel, transverse to the axis of the vessel, illustrating the precession of the distal end of the medical device.

As shown in FIG. 5, the user identifies a location on the vessel tree, for example by pointing a cursor on a display, at a point a little ahead of (distal to) the expected location of the distal end of the medical device. As shown in FIG. 6, the point A is the clicked or selected point in a branch, and the actual distal end of the device may be proximal to the branch. The software computes the field direction based on vessel geometry, and preferably also taking into account the specific characteristics of the medical device, such as stiffness, etc. A length of the vessel centerline is chosen for this calculation, as explained more fully below. This length could be highlighted on the display for clarity.

Any steering requires knowledge of the length of the device to be steered and its associated geometry. The centerline of the vascular tree is divided by a plurality of fairly closely spaced nodes (FIG. 4). For convenience, it may be desirable to assign a unique label or index to each branch or vessel segment, and to also label its parent (if any). A unique (unit) tangent vector can be assigned to each node that is not a branch node. For example, where i−1, i, and i+1, are three successive nodes ordered proximal to distal, $$\vec{t}_i' = \frac{(\vec{x}_{i+1} - \vec{x}_i)}{|\vec{x}_{i+1} - \vec{x}_i|} + \frac{(\vec{x}_i - \vec{x}_{i-1})}{|\vec{x}_i - \vec{x}_{i-1}|}$$

$$\vec{t}_i = \vec{t}_i' / |\vec{t}_i'|$$

For an end node (like the most proximal or a distal node at the end of a branch), the local tangent vector is:

$$\vec{t}_i = \frac{(\vec{x}_{i+1} - \vec{x}_i)}{|x_{i+1} - \vec{x}_i|}$$

for a proximal end node, and:

$$\vec{t}_i = \frac{(\vec{x}_i - \vec{x}_{i-1})}{|x_i - \vec{x}_{i-1}|}$$

for a distal end node.

For every branch node, a (unit) tangent vector is assigned for each of the branches. For example, as shown in FIG. 4, "i" is the branch node leading to branches M and N. j is the first node uniquely on branch M, and k is the first node uniquely on branch N.

$$\vec{t}_{i,M}' = \frac{(\vec{x}_j - \vec{x}_i)}{|\vec{x}_j - \vec{x}_i|} + \frac{(\vec{x}_i - \vec{x}_{i-1})}{|\vec{x}_i - \vec{x}_{i-1}|}$$

$$\vec{t}_{i,N}' = \frac{(\vec{x}_k - \vec{x}_i)}{|\vec{x}_l - \vec{x}_i|} + \frac{(\vec{x}_i - \vec{x}_{i-1})}{|\vec{x}_i - \vec{x}_{i-1}|}$$

then $$\vec{t}_{i,M} = \vec{t}_{i,M}' / |\vec{t}_{i,M}'|$$

$$\vec{t}_{i,N} = \vec{t}_{i,N}' / |\vec{t}_{i,N}'|$$

are the unit tangents at branch node i, assigned to branches M and N respectively.

If node n is selected by the user as a desired target destination, starting from node n the system backtracks at least a distance $L_o$. In the preferred embodiment, $L_o$ is about 25-26 mm. This results in a set of nodes. The nodes are indexed (from proximal to distal) by p. For each node p in the set, the curvature vector is given as:

$$\vec{c}_p = \frac{(\vec{t}_{p+1} - \vec{t}_{p-1})}{\{|\vec{x}_{p=1} - \vec{x}_p| + |\vec{x}_p - \vec{x}_{p-1}|\}}$$

If a branch node is encountered, a suitable local tangent is selected based on the label of the distal branch (e.g. M or N in this description). For an end node, the proximal end curvature vector is given by:

$$\vec{c}_p = \frac{(\vec{t}_{p+1} - \vec{t}_p)}{|\vec{x}_{p+1} - \vec{x}_p|}$$

and the distal end curvature vector is given by:

$$\vec{c}_p = \frac{(\vec{t}_p - \vec{t}_{p-1})}{|\vec{x}_p - \vec{x}_{p-1}|}$$

The distal end is this particular example is the user-selected node n.

The result is a set of smoother curvatures defined along the set of nodes p. Starting from node j, moving back along the nodes until a local curvature maximum is found, at a node m such that:

$$|\vec{c}_m| > |\vec{c}_{m-1}|$$

and $$|\vec{c}_m| > |\vec{c}_{m+1}|.$$

The length of the nodes from n to the local maximum m is:

$$l_m = |\vec{x}_{m+1} - \vec{x}_m| + |\vec{x}_{m+2} - \vec{x}_{m+1}| + \ldots + |\vec{x}_n - \vec{x}_{n-1}|$$

If no local maximum is found, then L, the length modeled, is $L = L_o$ and k', the node from which the device is modeled, is k'=1.

Selecting $L_1$, the minimum length of the device to be modeled, as $L_1=6$ mm, and $L_2$, an additional length to ensure that there is sufficient length for the device being modeled, as $L_2=6$ mm. If $l_m<L_1$, then L is increased an additional length $L_2$, otherwise, $L=l_m$ and $k'=m$. Then:

$$\vec{n}' = \sum_{k=k'}^{n} (\vec{t}_k \times \vec{c}_k)$$

and $$\vec{n} = \vec{n}'/|\vec{n}'|$$

where $\vec{n}$ is the smoothed normal to the effective bending plane of the device.

$\vec{t}_{k'}$ is the unit tangent to the base of the device and $\vec{t}_n$ is the unit tangent at the tip. Define the tip deflection angle $\theta$ as:

$$\theta = \cos^{-1}(\vec{t}_{k'} \cdot \vec{t}_n)$$

L as the length of the distal portion of the device, and $\beta(L)$ as its effective stiffness. The latter can be implemented as a C++ function, where $\beta(L)$ is defined as $$\frac{1}{C(L)};$$

where $$C(L) \equiv \int_0^L \frac{ds}{EI(s)}$$

where E is Young's Modulus and $$I(s) = \frac{\pi}{4} r^4(s).$$

For the specific case of a magnetic embodiment, the desired field unit vector can be determined as follows:

Let m be the magnetic moment of the tip magnet and B be the field strength, $$\alpha = \frac{\beta(L) \cdot \theta}{mB}$$

where m is in Amp-meter$^2$, B is in Tesla, $\theta$ is in radians, and $\beta(L)$ is in N-m. If $$\alpha > 1, \text{ let } \psi = \theta + \frac{\pi}{2} \text{ else } \psi = \theta + \sin^{-1}(\alpha).$$

Construct a 3×3 rotation matrix $R \equiv R_{\vec{n}}(\psi)$=rotation matrix by an angle $\psi$ about the axis defined by $\vec{n}$. Then $\vec{u}_B = R \vec{t}_{k'}$ is the desired (unit) field vector.

Precession

As described above, in some circumstances it is desirable to precess the distal end of the medical device about the axial centerline of the vessel. The plane of the precession of the tip is perpendicular to the vessel axis $\vec{a}$, where $\vec{n}$ is the normal to the bending plane of the device.

Define $\vec{p} \equiv \vec{n} \times \vec{a}$, and construct a reference line in the precession plane in the superior direction. If $\vec{s}$=superior direction unit vector, define $\vec{q}' \equiv \vec{s} - \vec{a}(\vec{s} \cdot \vec{a})$ and $$\vec{q} = \frac{\vec{q}'}{|\vec{q}'|},$$

the reference line unit vector and also define $\phi = \cos^{-1}(\vec{p} \cdot \vec{q}) \cdot [-\text{sign}(\vec{n} \cdot \vec{q})]$.

In the precession mode, it may be desirable to constrain the angular range of precession to be about $\gamma<30°$. Let (x,y) label a selected spot in the precession plane, where x and y are polar angles. Define $x'=x \cos \phi + y \sin \phi$ and $y'=-x \sin \phi + y \cos \phi$ where y' is the additional tip deflection angle, and x' is the device rotation angle (about the base). (x', y') are respectively equivalent rotation and deflection angles for the selected spot (x, y) in the precession plane. Recall that $\theta = \cos^{-1}(\vec{t}_{k'} \cdot \vec{t}_n)$. Defining $\theta'$, the deflection with precession, as $\theta'=\theta+y'$ then $$\alpha = \frac{\beta(L) \theta'}{mB}.$$

If $\alpha < \pi/2$, map the selected polar angle (x, y) to respectively device rotation and deflection angles x' and $\psi'=\theta'+\sin^{-1}(\alpha')$, otherwise let $$\psi' = \theta' + \frac{\pi}{2}.$$

The desired field direction for the selected spot is then:

$$|R_{\vec{t}_{k'}}(-x') R_{\vec{n}}(\psi')| \vec{t}_{k'}$$

where $R_{\vec{t}_{k'}}(-x')$ represents the rotation by angle (−x') about $\vec{t}_{k'}$, and $R_{\vec{n}}(\psi')$ represents the rotation by angle ($\psi'$) about $\vec{n}$.

Define $M \equiv R \vec{t}_{k'}(-x') R_n(\psi')$. Sequential precession over a set of field directions is performed as follows. If i labels the currently identified (presently applied) location of the distal end of the device in the precession plane, and one desires to move to a new location (i+1), apply a rotation $N \equiv (M_{i+1} M_i^T)$ to the current field vector.

Figure 8:
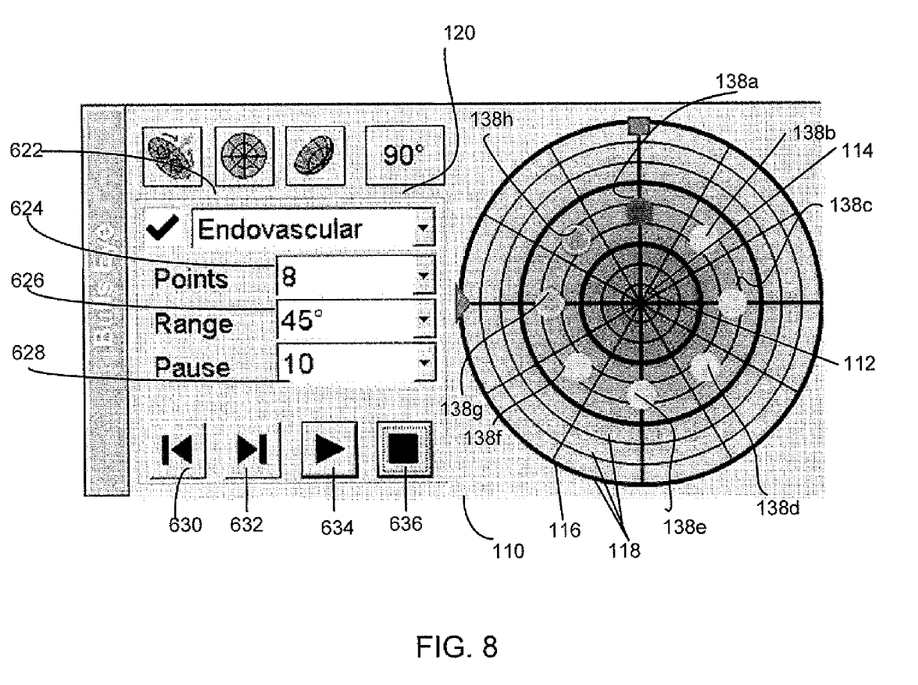
FIG. 8 is a schematic diagram of a screen display for controlling the precession of the distal tip.

A control interface of the third embodiment is illustrated in FIG. 8. This control operates a magnetic navigation system that applies a magnetic field in a selected direction to an operating region in a subject to magnetically orient a medical device in the operating region. The interface facilitates the specification of the direction of the magnetic field to be applied by the magnetic navigation system, and includes a display pane 110 on which a representation 112 of the current orientation of the medical device (or the currently applied magnetic field) is displayed. In this preferred embodiment the representation 112 is a dot 114 at the center of a circular grid 116 comprising a plurality of concentric circles 118 representing angular deflections from the axis of the medical device. The display pane 110 also includes a selector 120 for selecting one of a plurality of predetermined patterns of new orientations. The interface includes an input device for selecting one of the plurality of patterns of new orientations. This input device may be a mouse and/or a keyboard for operating the selector. Of course, some other input device, such as a joystick, touch screen, etc. could be used for selecting a pattern, The selector 120 includes a pick box 122 for selecting the type of pattern. In this preferred embodiment there are preferably at least two types of patterns, a circular pattern generally concentric about the current position of the medical device, and a spiral pattern originating at the current position of the medical device. The selector preferably also includes a pick box 124 for selecting the number of positions in the pattern. The selector preferably also includes a pick box 126 for selecting the angular displacement of the pattern from the current position. The selector may also include a pick box 128 for selecting the delay between movement among the positions in the patter. Lastly, the selector 120 can include a previous position virtual button 130, a next position virtual button 132, a play virtual button 134, and a stop virtual button 136.

The user selects the type of pattern in pick box 122, the number of positions in the pattern in pick box 124, the angular displacement of the pattern in pick box 126, and if desired a delay time in pick box 128. The selected pattern is displayed on the circular grid 116 as a plurality of dots 138. The user can then operate the magnetic navigation system by clicking on the virtual buttons 130, 132, 134, and 136. Operating button 130 causes the interface to operate the magnetic navigation system to the previous position in the pattern. Operating virtual button 132 causes the interface to operate the magnetic navigation system to the next position in the pattern. Operating the virtual button 134 causes the interface to operate the magnetic navigation system to successively move to each position in the pattern. Operating the virtual button 134 stops automatic operation of the interface.

The colors of the representations of the positions 138 in the pattern preferably indicate the status of each position. For example, as shown in FIG. 8A, the dots 138b-138h can be a first color (e.g. light grey), indicating that the medical device has not yet been operated to those positions. The dot 138a can be a second color (e.g. yellow), indicating it is the current position of the medical device. As shown in FIG. 8 the dots 138b-138h can be in a first color, the dot 138a can be in a second color and a dot of a third color (e.g. green) indicating the movement of the field appears behind dot 138a. As shown in FIG. 8, dot 138a is a fourth color (e.g. dark grey) indicating that the medical device has already been navigated to the position, the dot 138h is not the second color, indicating it is the current position of the medical device, and dots 138b-138g are the first color, indicating that the medical device still has not been navigated to these positions.

This pattern navigation, and automated pattern navigation, make it easy to navigate the medical device for selected procedures. For example in mapping procedures, wherein it is desirable to move a mapping catheter to trace an electrical signal, automated movement in a circular or spiral or other pattern facilitates the mapping procedure. Similarly, in ablation procedures, where the user needs to move the tip of an ablation catheter to form a closed loop of ablation, automated movement in a circular or other patter facilitates the ablation procedure.

In operation the user can use the interface to operate a magnetic navigation system to apply a magnetic field in a selected direction in an operating region in a subject, to magnetically orient a medical device in the operating region. The user selects one of a plurality of predetermined patterns of new positions for the medical device using the selector 120 and an input/output device, such as a mouse. The user then simply manually operates the magnetic navigation system to successively orient the medical device in each new position of the pattern by operating virtual button 132 or initiate the system automatically moving from position to position after the predetermined delay by operating virtual button 134.

What is claimed:

1. A method of operating a navigation system that can orient the distal end of a medical device in a selected direction at a plurality of intervals along a portion of a body lumen, to navigate the medical device through a portion of a body lumen in an operating region in a subject, the method comprising:
using a computer to perform the following steps:
identifying a plurality of spaced apart nodes that define a centerline along a desired path through a portion of the body lumen in the operating region;
selecting a node from the plurality of spaced apart nodes as a desired target location on the identified path;
backtracking at least a predetermined distance from the selected node, such that a length of the centerline is chosen for calculation of a deflection angle;
selecting a set of nodes within the predetermined distance preceding the selected node;
determining the distal end location of the medical device;
determining a distal end deflection angle at which to orient the distal end of the medical device based on the selected set of nodes, to obtain a good alignment of the distal end with the centerline of the path; and
computing control variables, based on the determined distal end deflection angle, that are applied to the navigation system to operate the navigation system to orient the distal end of the medical device in a direction along the path and advancing the distal end of the medical device; and
repeating the steps of determining the distal end location, determining a distal end deflection angle, and computing control variables for operating the navigation system for orienting the distal end at a plurality of intervals along the body lumen, to navigate the medical device through the body lumen.

2. The method according to claim 1 wherein the centerline along the desired path is identified by identifying points on the path on at least two images of the operating region.

3. The method according to claim 1 wherein the centerline along the desired path is identified by identifying lines on the path on at least two images of the operating region.

4. The method according to claim 1 where the centerline along the desired path is determined from an idealized anatomical model.

5. The method according to claim 1 where the centerline along the desired path is determined from a three dimensional dataset.

6. The method of claim 1 where the selection of the node as the desired target location on the path is done by determining the current location of the distal end of the medical device.

7. The method according to claim 6 wherein the current location of the distal end of the medical device is determined from image processing.

8. The method according to claim 6 wherein the current location of the distal end of the medical device is determined with a localization system.

9. The method according to claim 6 wherein the current location of the distal end of the medical device is determined with a length tracking system.

10. The method according to claim 1 wherein the distal end of the medical device is advanced by manually advancing the proximal end of the medical device.

11. The method according to claim 1 wherein the distal end of the medical device is advanced with a machine that advances the proximal end of the medical device.

12. The method according to claim 11 wherein the steps of computing control variables for operating the navigation system to orient the distal end of the medical device in a direction along the path and advancing the distal end of the medical device comprises:

repeatedly determining the location of the distal end of the medical device and orienting the medical device at the determined location to follow the determined path; and advancing the medical device.

13. The method according to claim 12 wherein the location of the distal end of the medical device is determined continuously.

14. The method according to claim 12 wherein the location of the distal end of the medical device is determined at predetermined time intervals.

15. The method according to claim 14 wherein the predetermined time intervals are dynamically adjusted depending upon the curvature of the path.

16. The method according to claim 14 wherein the speed of the advancement is controlled based upon the curvature of the path.

17. The method according to claim 12 wherein the location of the distal end of the medical device is determined at predetermined distance intervals, as determined from the advancement of the distal end of the medical device.

18. The method according to claim 17 wherein the predetermined distance intervals are dynamically adjusted depending upon the curvature of the path.

19. A method of operating in a stepwise mode a navigation system that can orient the distal end of a medical device in a selected direction at a plurality of intervals along a path through a portion of a body lumen, to navigate the medical device through a portion of a body lumen in an operating region in a subject, the method comprising:

(a) using a computer to perform the following steps:
(b) identifying a centerline of a path through an idealized model of the body lumen, where the centerline is defined by plurality of spaced apart nodes;
(c) selecting a node from the plurality of spaced apart nodes as a desired location on the path for device tip alignment with the path;
(d) backtracking at least a predetermined distance from the selected node, such that a length of the centerline is chosen for calculation of a deflection angle;
(e) selecting a set of nodes within the predetermined distance preceding the selected node;
(f) determining a deflection angle at which to orient the distal end of the medical device to obtain a good alignment with the centerline of the path, based on the selected set of nodes;
(g) computing control variables, based on the determined deflection angle, that are a lied to the navigation system to operate the navigation system to orient the distal end of the medical device in a direction along the path of the idealized model of the body lumen at the determined location and advancing the distal end of the medical device; and
(h) repeating steps (b) through (g) at a plurality of intervals along the portion of the body lumen as needed to navigate the medical device through the body lumen.

20. A method of operating a navigation system that can orient the distal end of a medical device in a selected direction at a plurality of intervals along a path through a portion of a body lumen, to navigate the medical device through a portion of a body lumen in an operating region in a subject, the method comprising:

(a) using a computer to perform the following steps:
(b) identifying a centerline of a path through a portion of the body lumen in the operating region, where the centerline is defined by plurality of spaced apart nodes;
(c) displaying a two-dimensional image of the operating region including the path through the body lumen;
(d) accepting via the two-dimensional image displayed a selection from the plurality of spaced apart nodes that is near a desired target in the portion of the body lumen in the operating region;
(e) backtracking at least a predetermined distance from the selected node, such that a length of the centerline is chosen for calculation of a deflection angle;
(f) selecting a set of nodes within the predetermined distance preceding the selected node;
(g) determining the current location of the distal end of the medical device;
(h) determining a deflection angle based on the selected set of nodes, which angle includes some amount of precession, for orienting the distal end of the medical device at the determined deflection angle with respect to the centerline of the path so as to orient the distal end other than along the centerline of the desired path;
(i) computing control variables, based on the determined deflection angle, that are applied to the navigation system to operate the navigation system to orient the distal end of the medical device in a direction at a predetermined angle with respect to the centerline of the path and advancing the distal end of the medical device.

21. The method according to claim 16 wherein the determined deflection angle changes for each of the plurality of intervals along the portion of the body lumen.

22. A method of operating in a continuous mode a navigation system that can orient the distal end of a medical device in a selected direction at a plurality of intervals along a path through a portion of a body lumen, to navigate the medical device through a portion of a body lumen in an operating region in a subject, the method comprising:

(a) using a computer to perform the following steps:
(b) identifying a centerline of a path through a portion of the body lumen in the operating region, where the centerline is defined by plurality of spaced apart nodes;
(c) displaying a two-dimensional image of the operating region including the path through the body lumen;
(d) selecting a node from the plurality of nodes as a desired target location on the path for device tip alignment with the path;
(e) backtracking at least a predetermined distance from the selected node, such that a length of the centerline is chosen for calculation of a deflection angle;
(f) selecting a set of nodes within the predetermined distance preceding the selected node, from which set of nodes a set of curvatures may be defined;

(g) determining a deflection angle at which to orient the distal end of the medical device to obtain a good alignment with the centerline of the path direction for a discrete interval based on the local degree of curvature in the selected set of nodes;

(h) computing control variables, based on the determined deflection angle, that are applied to the navigation system to operate the navigation system to orient the distal end of the medical device in a direction substantially aligned with the path direction at the discrete interval; and (i) automatically repeating steps (d) through (h) for the plurality of intervals along the portion of the body lumen as needed to automatically navigate the medical device through the body lumen.

23. A method of operating a navigation system that can orient the distal end of a medical device in a selected direction at a plurality of intervals along a path through a portion of a body lumen, to navigate the medical device through a portion of a body lumen in an operating region in a subject, the method comprising:

using a computer to perform the following steps:

determining a three dimensional configuration of the portion of the body lumen in the operating region;

displaying a two-dimensional image of the operating region including the portion of the body lumen;

accepting a selection from the two-dimensional display of a point on the portion of the body lumen in the operating region;

determining the corresponding three dimensional location of the point selected on the two dimensional display;

determining the current location of the distal end of the medical device;

defining a centerline of the path through the portion of a body lumen, where the centerline is defined by a plurality of spaced apart nodes;

backtracking at least a predetermined distance from the selected point on the portion of the body lumen, such that a length of the centerline is chosen for calculation of a deflection angle;

selecting a set of nodes within the predetermined distance preceding the selected node;

repeatedly determining a deflection angle based on the selected set of nodes, for orienting the distal end of the medical device to obtain a good alignment of the medical device with the centerline at a plurality of intervals along the path through the body lumen from the current location of the distal end of the medical device to the three dimensional location corresponding to the point selected on the two dimensional display; and computing control variables, based on the determined deflection angle, that are applied to the navigation system to operate the navigation system to repeatedly orient the distal end of the medical device in a direction along the path at the plurality of intervals, and advancing the distal end of the medical device.

24. The method according to claim 23 wherein the distal end of the medical device is advanced by manually advancing the proximal end of the medical device.

25. The method according to claim 23 wherein the distal end of the medical device is advanced with a machine that advances the proximal end of the medical device.

26. The method according to claim 23 wherein the steps of computing control variables for operating the navigation system to orient the distal end of the medical device in a direction along the path and advancing the distal end of the medical device comprises:

repeatedly determining the location of the distal end of the medical device and determining the orientation of the medical device in the determined location to follow the determined path; and advancing the medical device.

27. The method according to claim 23 wherein the location of the distal end of the medical device is determined continuously.

28. The method according to claim 23 wherein the location of the distal end of the medical device is determined at predetermined time intervals.

29. The method according to claim 23 wherein the location of the distal end of the medical device is determined at predetermined distance intervals, as determined from the advancement of the distal end of the medical device.

* * * * *

UNITED STATES PATENT AND TRADEMARK OFFICE
CERTIFICATE OF CORRECTION

PATENT NO.        : 7,627,361 B2                             Page 1 of 1
APPLICATION NO. : 11/211155
DATED             : December 1, 2009
INVENTOR(S)       : Raju R. Viswanathan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 648 days.

Signed and Sealed this

Second Day of November, 2010

David J. Kappos
*Director of the United States Patent and Trademark Office*